United States Patent [19]

Verniere et al.

[11] Patent Number: 4,835,163

[45] Date of Patent: May 30, 1989

[54] N-ALKOXYALKYL DERIVATIVES OF QUINOLONE CARBOXAMIDES

[75] Inventors: Jean-Claude Verniere; Jacques Simiand, both of Muret; Peter E. Keane, Toulouse, all of France

[73] Assignee: Sanofi, Paris, France

[21] Appl. No.: 3,567

[22] Filed: Jan. 15, 1987

[30] Foreign Application Priority Data

Jan. 24, 1986 [FR] France ............................... 86 01401

[51] Int. Cl.$^4$ ..................... C07D 215/56; A61K 31/47
[52] U.S. Cl. ......................................... 514/312; 546/156
[58] Field of Search ......................... 514/312; 546/156

[56] References Cited

U.S. PATENT DOCUMENTS 3,966,743  6/1976  Berger et al. ..................... 546/156

FOREIGN PATENT DOCUMENTS 12143    6/1969  Japan .
2167412  5/1986  United Kingdom .

OTHER PUBLICATIONS

Derwent Abstract for JP 44/12143, (6/2/69).

Primary Examiner—Anton H. Sutto
Assistant Examiner—E. Bernhardt
Attorney, Agent, or Firm—Wegner & Bretschneider

[57] ABSTRACT

The present invention concerns new derivatives of 4-oxo-1,4-dihydro-quinoline 3-carboxamide, answering to the following general formula:

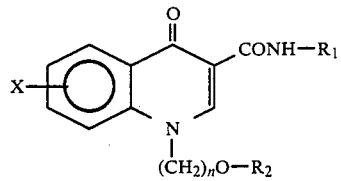

in which:
  $R_1$ represents a linear or branched lower alkyl radical, containing from 1 to 5 carbon atoms; an alkenyl or alkynyl radical containing from 2 to 5 carbon atoms; or a cycloalkyl radical containing from 3 to 5 carbon atoms,
  $R_2$ represents an alkyl radical containing from 1 to 4 carbon atoms, n is equal to 1 or 2,
  X represents a hydrogen, a halogen, a lower alkoxy or alkyl group.

The invention also concerns their application as medicaments and the compositions containing them.

8 Claims, No Drawings

N-ALKOXYALKYL DERIVATIVES OF QUINOLONE CARBOXAMIDES

The present invention concerns new derivatives of 4-oxo-1,4-dihydroquinoline 3-carboxamide, their preparation process, their application as medicaments and the compositions containing them.

The compounds of the invention answer to the general formula (I):

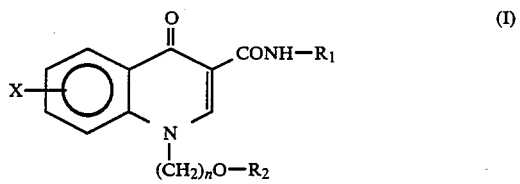

in which:

$R_1$ represents a linear or branched lower alkyl radical containing from 1 to 5 carbon atoms; an alkenyl or alkynyl radical containing from 2 to 5 carbon atoms; or a cycloalkyl radical containing from 3 to 5 carbon atoms, $R_2$ represents an alkyl radical containing from 1 to 4 carbon atoms, n is equal to 1 or 2, X represents a hydrogen, a halogen, an alkoxy or alkyl group with 1 to 4 carbon atoms.

The invention also includes the addition salts with pharmaceutically acceptable mineral or organic acids.

The compounds which are the subject of the present invention possess very useful pharmacological properties: they are endowed, in particular, with remarkable anticonvulsive and psychotonic properties. The subject of the invention is also a preparation process for compounds with the formula (I) characterized in that the compound with the formula (II):

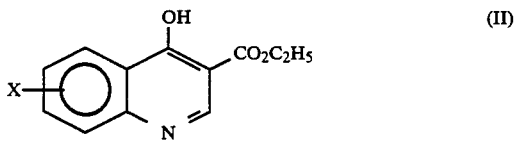

in which X has the same significances as in formula (I), is made to react with a halogenated derivative with the formula (III):

in which Y represents a halogen such as chlorine or bromine and n and $R_2$ have the same values as in formula (I), so as to obtain the compounds with the formula (IV):

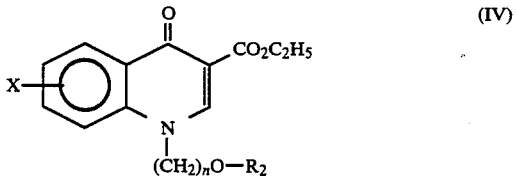

on which an amine with the formula (V):

in which $R_1$ has the same significances as in the formula (I), is made to react, so as to obtain the compound with the formula (I).

The quinolines with the formula (II) are known compounds: they can be prepared according to the process described by B. RIEGEL et al. (J. Am. Chem., Soc., 1949, 68, 1264–1266).

The compounds with the formula (IV) are obtained by heating the two reagents (II) and (III) at a temperature between 60° C. and 130° C., in the presence of a base such as potassium carbonate in an organic solvent such as dimethylformamide.

The fixing of the amine radical with the formula (V) on the compound with the formula (IV) is brought about by heating the reagents in an excess of the amine (V) at a temperature between 60° C. and 150° C., for a duration of 10 hrs to 48 hrs.

The reaction can be advantageously brought about by operating in a closed metallic reactor in such a way as to obtain by heating an internal pressure of 5 to 50 bars. In these conditions, the reagents (IV) and (V) are put to react in an organic solvent such as ethyl alcohol.

The following non-limiting examples are given as illustration of the present invention.

EXAMPLE 1

1-methoxymethyl-4-oxo-1,4-dihydro-quinoline 3-(N-propyl)carboxamide (I: $R_1=C_3H_7$; $R_2=CH_3$; n=1; X=H); derivative no. 1 (SR 25776)

(a) 1-methoxymethyl-4-oxo-1,4-dihydro-quinoline 3-(ethyl carboxylate) (IV: $R_2=CH_3$; X=H; N=1)

A mixture of 4-hydroxy-quinoline-3-(ethyl carboxylate) (II), 2 g (0.0092 mole) of potassium carbonate, 2 g (0.014 mole) in 20 ml of dimethylformamide is taken to 90° C. for 1 hour. After addition of 0.7 ml (0.0092 mole) of chloromethyl methylether (III) the heating is continued for 40 hours. After filtration and evaporation of the solvent, the residual crystals are washed with water and dried.

Colourless crystals, yield: 40%, m.p.=146° C.

Analysis: $C_{14}H_{15}NO_4$: Calculated: C 64.36; H 5.79; N 53.36; Found: C 64.15; H 5.89; N 5.17.

(b) 1-methoxymethyl-4-oxo-1,4-dihydro-quinoline 3-(N-propyl)carboxamide

A mixture of 1 g (0.0038 mole) of the product obtained in the previous stage and 28 ml of propylamine is taken to 80° C. for 24 hrs. After cooling, the crystals are filtered, washed with isopropyl ether and dried under vacuum.

Colourless crystals, yield: 70%, m.p.=159° C.

Analysis: $C_{15}H_{18}N_2O_3$: Calculated: C 65.68; H 6.61; N 10.21; Found: C 65.96; H 6.72; N 10.11.

EXAMPLE 2

1-methoxymethyl-4-oxo-1,4-dihydro-quinoline 3-(N-methyl) carboxamide (I: $R_1=CH_3$, $R_2=CH_3$, n=1, X=H); derivative no. 2 (SR 26004)

A mixture of 1-methoxymethyl-4-oxo-1,4-dihydro-quinoline 3-(ethyl carboxylate) (0.0038 mole) prepared according to example 1 and of methylamine at 33% in ethanol (150 ml) is heated at 130° C. for 8 hours in a reactor under a pressure of 40 bars. After evaporation of the solvent, the expected product is recrystallized from ethyl acetate:

Colourless crystals m.p.=205° C. (yield 37%)

Analysis: $C_{13}H_{14}N_2O_3$: Calculated: C 63.40; H 5.73; N 11.37; Found: C 63.38; H 5.76; N 11.14.

EXAMPLE 3

1-methoxymethyl-4-oxo-1,4-dihydro-quinoline 3-(N-ethyl)carboxamide (I: $R_1=C_2H_5$, $R_2=CH_3$, n=1, X=H) derivative no. 3 (SR25950)

This compound has been prepared following the operating method describe in example 2.

m.p.=190° C. (yield 40%)

Analysis: $C_{14}H_{16}N_2O_3$: Calculated: C 64.60; H 6.20; N 10.76; Found: C 64.29; H 6.10; 10.74.

The following examples have been prepared according to the operating method described in example 1.

EXAMPLE 4

1-methoxymethyl-4-oxo-1,4-dihydro-quinoline 3-(N-isopropyl)carboxamide. (I: $R_1=$

$R_2=CH_3$, n=1, X=H); derivative no. 4 (SR 25972)

m.p.=161° C. (yield 32%)

Analysis: $C_{15}H_{18}N_2O_3$; Calculated: C 65.68; H 6.61; N 10.21; Found: C 65.50; H 6.69; N 10.04.

EXAMPLE 5

1-methoxymethyl-4-oxo-1,4-dihydro-quinoline 3-(N-isobutyl)carboxamide. (I: $R_1=$

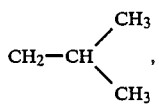

$R_2=CH_3$, n=1, X=H) derivative no. 5 (SR 25931)

m.p.=136° C. (yield 50%)

Analysis: $C_{16}H_{20}N_2O_3$: Calculated: C 66.65; H 6.93; N 9.71; Found: C 66.38; H 6.96; N 9.59.

EXAMPLE 6

1-methoxymethyl-4-oxo-1,4-dihydro-quinoline 3-(N-(propyne-2-yl))carboxamide (I: $R_1=CH_2-C\equiv CH$, $R_2=CH_3$, n=1, X=H) derivative no. 6 (SR 26080)

m.p.=213° C. (yield 43%)

Analysis: $C_{15}H_{14}N_2O_3$: Calculated: C 66.66; H 5.22; N 10.36; Found: C 66.93; H 5.28; N 10.31.

EXAMPLE 7

1-methoxymethyl-4-oxo-1,4-dihydro-quinoline 3-(N-cyclopropyl)carboxamide. (I: $R_1=$

$R_2=CH_3$, n=1, X=H) derivative no. 7 (SR 26075)

m.p.=200° C. (yield 46%)

Analysis: $C_{15}H_{16}N_2O_3$: Calculated: C 66.16; H 5.92; N 10.29; Found: C 65.93; H 5.90; N 9.95.

EXAMPLE 8

1-methoxymethyl-4-oxo-1,4-dihydro-quinoline 3-(N-cyclopentyl)carboxamide. (I: $R_1=$

$R_2=CH_3$, n=1, X=H) derivative no. 8 (SR 26029)

m.p.=155° C. (yield 55%)

Analysis: $C_{17}H_{20}N_2O_3$: Calculated: C 67.98; H 6.71; N 9.33; Found: C 68.12; H 6.73; N 9.29.

EXAMPLE 9

1-methoxymethyl-4-oxo-6-fluoro-1,4-dihydro-quinoline 3-(N-propyl)carboxamide (I: $R_1=C_3H_7$, $R_2=CH_3$, n=1, X=F) derivative no. 9 (SR 26049)

m.p.=162° C. (yield 50%)

Analysis: $C_{15}H_{17}FN_2O_3$: Calculated: C 61.64; H 5.86; N 9.58; Found: C 61.62; H 5.91; N 9.34.

This compound has been prepared according to the operating method described in example 1 starting from 1-methoxymethyl-4-oxo-6-fluoro-1,4-dihydro-quinoline 3-(ethyl carboxylate) (IV: $R_2=CH_3$, n=1, X=F; m.p.=170° C. (yield 50%).

EXAMPLE 10

1-methoxymethyl-4-oxo-8-fluoro-1,4-dihydro-quinoline 3-(N-propyl)carboxamide (I: $R_1=C_3H_7$, $R_2=CH_3$, n=1, X=F) derivative no. 10 (SR 26109)

m.p.=134° C. (yield 67%)

Analysis: $C_{15}H_{17}FN_2O_3$: Calculated: C 61.64; H 5.86; N 9.58; Found: C 61.65; H 5.68; N 9.45.

This compound has been prepared according to the operating method described in example 1 starting with 1-methoxymethyl-4-oxo-8-fluoro-1,4-dihydro-quinoline 3-(ethyl carboxylate) (IV: $R_2=CH_3$, n=1, X=F; m.p.=142° C; yield 44%).

EXAMPLE 11

1-methoxymethyl-4-oxo-8-chloro-1,4-dihydro-quinoline 3-(N-propyl)carboxamide (I: $R_1=C_3H_7$, $R_2=CH_3$, n=1, X=Cl) derivative no. 11 (SR 26117)

m.p.=152° C. (yield 40%)

Analysis: $C_{15}H_{17}ClN_2O_3$: Calculated: C 58.35; H 5.55; N 9.07; Found: C 58.52; H 5.57; N 8.97.

This compound has been prepared according to the operating method described in example 1 with 1-methoxymethyl-4-oxo-8-chloro-1,4-dihydro-quinoline 3-(ethyl carboxylate) (IV: $R_2=CH_3$, n=1, X=Cl; yield 35%).

EXAMPLE 12

1-methoxymethyl-4-oxo-6-methoxy-1,4-dihydro-quinoline 3-(N-propyl)carboxamide (I: $R_1=C_3H_7$, $R_2=CH_3$, n=1, X=OCH$_3$) derivative no. 12 (SR 25896)

m.p.=200° C. (yield 50%)

Analysis: $C_{16}H_{20}N_2O_4$: Calculated: C 63.14; H 6.62; N 9.21; Found: C 63.02; H 6.67; N 9.14.

This compound has been prepared according to the operating method described in example 1 starting with 1-methoxymethyl-4-oxo-6-methoxy-1,4-dihydro-quinoline 3-(ethyl carboxylate) (IV: $R_2=CH_3$, $n=1$, $X=OCH_3$; m.p.$=149°$ C., yield 30%).

EXAMPLE 13

1-ethoxymethyl-4-oxo-1,4-dihydro-quinoline 3-(N-propyl)carboxamide (I: $R_1=C_3H_7$, $R_2=C_2H_5$, $n=1$, $X=H$) derivative no. 13 (SR 25983)

1. 1-ethoxymethyl-4-oxo-1,4-dihydro-quinoline 3-(ethyl carboxylate) (IV: $R_2=C_2H_5$, $n=1$, $X=H$)

A mixture of 4-hydroxy-quinoline 3-(ethyl carboxylate) (4 g 0.016 mole) and of potassium carbonate (3.5 g 0.025 mole) in dimethylformamide (40 ml) is taken to 90° C. for 30 minutes. After addition of chloromethylethylether (1.93 ml, 0.021 mole), heating is continued for 30 hours. After filtration and evaporation of the solvent the expected product is washed with water and dried; Colourless crystals; m.p.$=64°$ C.; (yield 89%).

2. 1-ethoxymethyl-4-oxo-1.4-dihydro-quinoline 3-(N-propyl)carboxamide.

The product obtained in the previous stage (2 g, 0.00726 mole) in solution in propylamine (60 ml) is taken to 80° C. for 20 hours. The expected product crystallizes cold. It is washed with isopropyl ether and dried; Colourless crystals; m.p.$=150°$ C. (yield 80%).

Analysis: $C_{16}H_{20}N_2O_3$: Calculated: C 66.65; H 6.99; N 9.72; Found: C 66.27; H 7.18; N 9.52.

EXAMPLE 14

1-ethoxyethyl-4-oxo-1,4-dihydro-quinoline 3-(N-propyl)carboxamide (I: $R_1=C_3H_7$, $R_2=C_2H_5$, $n=2$, $X=H$) derivative no. 14 (SR 26002)

1. 1-ethoxyethyl-4-oxo-1,4-dihydro-quinoline 3-(ethyl carboxylate) (IV: $R_2=C_2H_5$, $n=2$, $X=H$)

A mixture of 4-hydroxy quinoline 3-(ethyl carboxylate) (5 g, 0.02 mole) and of potassium carbonate (4.38 g, 0.0308 mole) in dimethylformamide (60 ml) is taken to 90° C. for 30 minutes. After addition of bromoethylethylether (2.9 ml, 0.026 mole), heating is maintained for 20 hours. After filtration and evaporation of the solvent, the expected product is washed with water: Colourless crystals, m.p.$=107°$ C. (yield 96%)

2. 1-ethoxyethyl-4-oxo-1,4-dihydro quinoline 3-(N-propyl)carboxamide

A mixture of the previous product (2 g, 0.0069 mole) and of propylamine (120 ml) is taken to 80° C. for 48 hours. After evaporation the expected product is chromatographed on a silica column with ethyl acetate: Colourless crystals; m.p.$=116°$ C. (yield 45%).

Analysis: $C_{17}H_{22}N_2O_3$: Calculated: C 67.53; H 7.33; N 9.26; Found: C 67.62; H 7.49; N 9.11.

EXAMPLE 15

1-methoxyethyl-4-oxo-1,4-dihydro-quinoline 3-(N-propyl)carboxamide (I: $R_1=C_3H_7$, $R_2=CH_3$, $n=2$, $X=H$) derivative no. 15 (SR 26068)

m.p.$=114°$ C. (yield 28%)

This compound has been prepared according to the operating method described in example 14 starting with 1-methoxyethyl-4-oxo-1,4-dihydro quinoline 3-(ethyl carboxylate) (IV: $R_2=CH_3$, $n=2$, $X=H$; m.p.$=140°$ C., yield 40%).

Analysis: $C_{16}H_{20}N_2O_3$: Calculated: C 66.64; H 6.99; N 9.72; Found: C 66.72; H 7.25; N 9.80.

The results of the toxicological and pharmacological tests cited hereafter, have enabled the useful properties of the invention to be brought to the fore, in particular, the anticonvulsive and psychotonic properties.

The subject of the invention is therefore a medicament having in particular anticonvulsive and psychotonic activities characterized in that they contain as active ingredient a derivative with the formula (I) or an addition salt with a therapeutically acceptable mineral or organic acid.

Toxicological study

The components of the invention benefit from a good tolerance and a weak toxicity. As an indication, the LD 50 for the oral route is 1100 mg/kg for derivative no. 1, in mice.

The tests carried out on various animal species for toxicity, acute, subchronic and chronic, have not brought out any local or general reaction, disturbance or anomaly in the biochemical, macroscopic and microscopic examinations carried out all through the tests.

Pharmacological study (1) Anticonvulsive activity

This activity has been studied by the test with pentetrazol, according to the method of EVERETT and RICHARDS (J. Pharm. Exp. Ther. 1944, 81, 402–407).

The product under test is administered by oral route to groups of 10 mice (male CD1, 20–25 g) 30 minutes before administration of pentetrazol by sub-cutaneous route, at a dose of 135 mg/kg. The number of animals in each group who do not show a tonic attack during the 30 minutes following the administration of the convulsive agent is noted. Thus the DE50 is determined, which is the dose which avoids the appearance of attacks in half of the animals. The DE 50 has been calculated by the method of D. K. Finney (Probit analysis; University Press; Cambridge; 1971).

The results are recorded in the following table:

| derivative number | $DE_{50}$ (mg/Kg) |
| --- | --- |
| 1 | 55 |
| 5 | 46 |
| 7 | 67 |
| 8 | 108 |
| 9 | 62 |
| 10 | 53 |
| 11 | 21 |
| 12 | 65 |
| 13 | 75 |
| 14 | 79 |
| 15 | 50 |
| sodium valproate | 200 |
| phenobarbital | 10 |

(2) Locomotive activity

This activity has been studied according to the method of J. Boissier (Arch. Int. Pharmacodyn., 1965, 158, 212–221). The mice (male CD1 20–25 g) are placed in groups of three in the cages of a photoelectric cell actimeter. After 30 minutes of getting used to the enclosure, the animas are treated by oral route with the product under test in suspension in carboxymethylcellulose at 1%. A control set of untreated mice receive only the vehicle. Each set contains 12 groups of 3 mice. The movement activity responses are recorded for 80 minutes.

The results are shown in the following table:

|  | Doses mg/kg O.R. | Movement Activity for 80 min | P (Student test) |
| --- | --- | --- | --- |
| Untreated mice | 0 | 553 ± 200 | |
| Mice treated by derivative no. 1 | 32 | 1842 ± 470 | <0.05 |
| Untreated mice | 0 | 1340 ± 159 | |
| Mice treated by derivative no. 3 | 32 | 3070 ± 219 | <0.05 |

(3) Antagonist activity vis a vis the hypnotic effects of benzodiazepines

This activity has been studied according to the method of J. Janssen (J. Med. Pharm. Chem., 1959, 1, 281–297).

The products of the invention, placed in suspension in carboxymethylcellulose at 1% were administered by intraperitoneal route to sets of 10 mice (male CD1, 20–25 g). Benzodiazepine (diazepam) was administered by intraperitoneal route 15 minutes after the compounds of the invention. A control group received carboxymethylcellulose before diazepam. The hypnotic effect was judged by noting in each set, the time during which the animals lost the standing-up reflex.

RESULTS

| Derivative SR | Dose (mg/kg i.p.) | Diazepam Dose (mg/kg i.p.) | Length of sleep in min |
| --- | --- | --- | --- |
| control | 0 | 6 | 97 ± 12 |
| derivative no. 1 | 25 | 6 | 39 ± 20* |
| derivative no. 7 | 25 | 6 | 32 ± 11* |
| derivative no. 9 | 25 | 6 | 22 ± 8* |
| derivative no. 3 | 25 | 6 | 9 ± 4* |
| derivative no. 5 | 25 | 6 | 62 ± 10* |

*P < 0.05 in relation to control set: test "t" of Student.

The toxicological and pharmacological studies which have just been given show the weak toxicity of the compounds of the invention and their good tolerance, as well as their interesting properties which make them very useful in human and veterinary therapeutics, and justify their use as medicaments.

The medicament of the invention can be presented for oral administration in the form of tablets, sugar-coated tablets, capsules, drops, granules or syrup.

It can also be presented for rectal administration in the form of suppositories and for parenteral administration in the form of injectable solution.

Each unitary dose contains, advantageously, from 5 mg to 300 mg of active principle, the doses which can be administered daily varying from 5 mg to 300 mg of active principle in relation to the age of the patient and the seriousness of the affection treated.

A few pharmaceutical formulations of the medicament of the invention will be given hereafter, as non-limiting examples:

(1) Tablets
derivative no. 1: 0.030 g
excipient: wheat starch, lactose, colloidal silica, talc, magnesium stearate.

(2) Sugar-coated tablets
derivative no. 11: 0.015 g
excipient: polyvinyl pyrrolidone, sodium carboxymethylcellulose,, magnesium stearate, levilite, hydroxypropylmethylcellulose titanium oxide, white wax.

(3) Capsules
derivative no. 3: 0.100 g
excipient: talc, lactose, magnesium stearate.

(4) Suppositories
derivative no. 10: 0.050 g
excipient: semi-synthetic triglycerides (5) Injectable solution
derivative no. 15: 0.025 g
excipient: isotonic solvent q.s.p. 3 ml Possessing interesting anticonvulsive and psychotonic properties and endowed with a good tolerance, the medicament of the invention is indicated for both adults and children in the treatment of convulsions, functional asthenias, memory and attention defects and also as an agent facilitating the re-awakening of a patient anesthetized by benzodiazepines.

What is claimed is:

1. Compounds with the formula

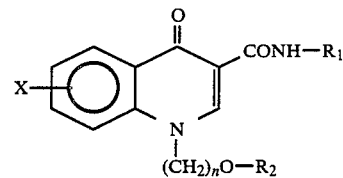

in which:

$R_1$ represents a group selected from a lower alkyl radical selected from linear and branched alkyl radicals containing from 1 to 5 carbon atoms; an alkenyl radical containing from 2 to 5 carbon atoms; an alkynyl radical containing from 2 to 5 carbon atoms; and a cycloalkyl radical containing from 3 to 5 carbon atoms, $R_2$ represents an alkyl radical containing from 1 to 4 carbon atoms, n represents an integer selected from the group consisting of 1 and 2, X represents a group selected from a hydrogen atom, a halogen atom, an alkoxy group containing from 1 to 4 carbon atoms and an alkyl group containing from 1 to 4 carbon atoms.

2. 1-methoxymethyl-4-oxo-1,4-dihydro-quinoline 3-(N-propyl)carboxamide and its salts of pharmaceutically acceptable acids selected from mineral acids and organic acids.

3. 1-methoxymethyl-4-oxo-1,4-dihydro-quinoline 3-(N-ethyl)carboxamide and its salts of pharmaceutically acceptable acids selected from mineral acids and organic acids.

4. 1-methoxymethyl-4-oxo-1,4-dihydro-quinoline 3-(N-isobutyl)carboxamide and its salts of pharmaceutically acceptable acids selected from mineral acids and organic acids.

5. 1-methoxymethyl-4-oxo-6-fluoro-1,4-dihydro-quinoline 3-(N-propyl)carboxamide and its salts of pharmaceutically acceptable acids selected from mineral acids and organic acids.

6. A pharmaceutical composition having anticonvulsant activity comprising an effective amount of a compound of claim 1 or its pharmaceutically acceptable salts in admixture with a pharmaceutical excipient.

7. A pharmaceutical composition according to claim 6 in unit dosage form.

8. A pharmaceutical composition according to claim 7 comprising unit doses containing from 0.05 g to 0.300 g of a compound according to claim 1 as active ingredient.

* * * * *